US006343601B1

(12) United States Patent
Kiske et al.

(10) Patent No.: US 6,343,601 B1
(45) Date of Patent: Feb. 5, 2002

(54) MOBILE MEDICAL SUPPLY DEVICE

(75) Inventors: Siegfried Kiske, Krummesse; Hans-Karsten Reimers, Hamberge, both of (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/504,686

(22) Filed: Feb. 15, 2000

(30) Foreign Application Priority Data

Jun. 24, 1999 (DE) ........................................ 199 28 835

(51) Int. Cl.[7] .............................................. A61M 15/00

(52) U.S. Cl. ............................ 128/203.12; 128/200.24; 248/647

(58) Field of Search ....................... 128/203.12, 200.24, 128/204.18; 248/129, 317, 636, 637, 647; 211/86.01, 97, 113

(56) References Cited

U.S. PATENT DOCUMENTS 5,306,109 A 4/1994 Kreuzer et al.
5,526,245 A * 6/1996 Davis et al. ................ 362/233
5,640,781 A * 6/1997 Carson et al. ................. 34/97
5,971,572 A * 10/1999 Rouchon et al. ............ 362/404

FOREIGN PATENT DOCUMENTS

DE 87 16 928 U1 6/1989
WO WO 96/35 403 11/1996

* cited by examiner

*Primary Examiner*—Glenn K. Dawson
(74) *Attorney, Agent, or Firm*—McGlew and Tuttle, P.C.

(57) ABSTRACT

A mobile medical supply device with a supply apparatus, especially an anesthesia apparatus, with a plurality of supply and drain lines. To make simple handling possible in connection with the moving along of the supply and drain lines during the movement of the supply apparatus (12) and to make it at the same time possible to install the entire device simply and inexpensively, the supply apparatus (12) can be moved on rollers (14) and a ceiling fixture (2) with a rotatably suspended multilink arm (4) is provided, which arm carries a frame (8) at its end away from the axis of rotation of the ceiling fixture (2), so that the frame (8) is movable due to the rotation of the multilink arm (4) and the pivoting of the links (5, 6) of the arm in relation to one another. Furthermore, a mechanical connection (10) is provided between the supply apparatus (12) and the frame (8), and the connection (10) has clearance for vertical movements between the frame (8) and the supply apparatus (12), so that unevennesses of the floor can be compensated during the movement of the supply apparatus (12) without load on the ceiling fixture. The frame (8) is provided with a supply and drain lines suspending apparatus. The supply apparatus (12) of the device can thus be moved and supply and drain lines suspended on the frame (8) are carried automatically and simple handling is thus possible. At the same time, the ceiling fixture (2) may be designed as a simple and inexpensive ceiling fixture because of the low load to which it is subjected.

10 Claims, 1 Drawing Sheet

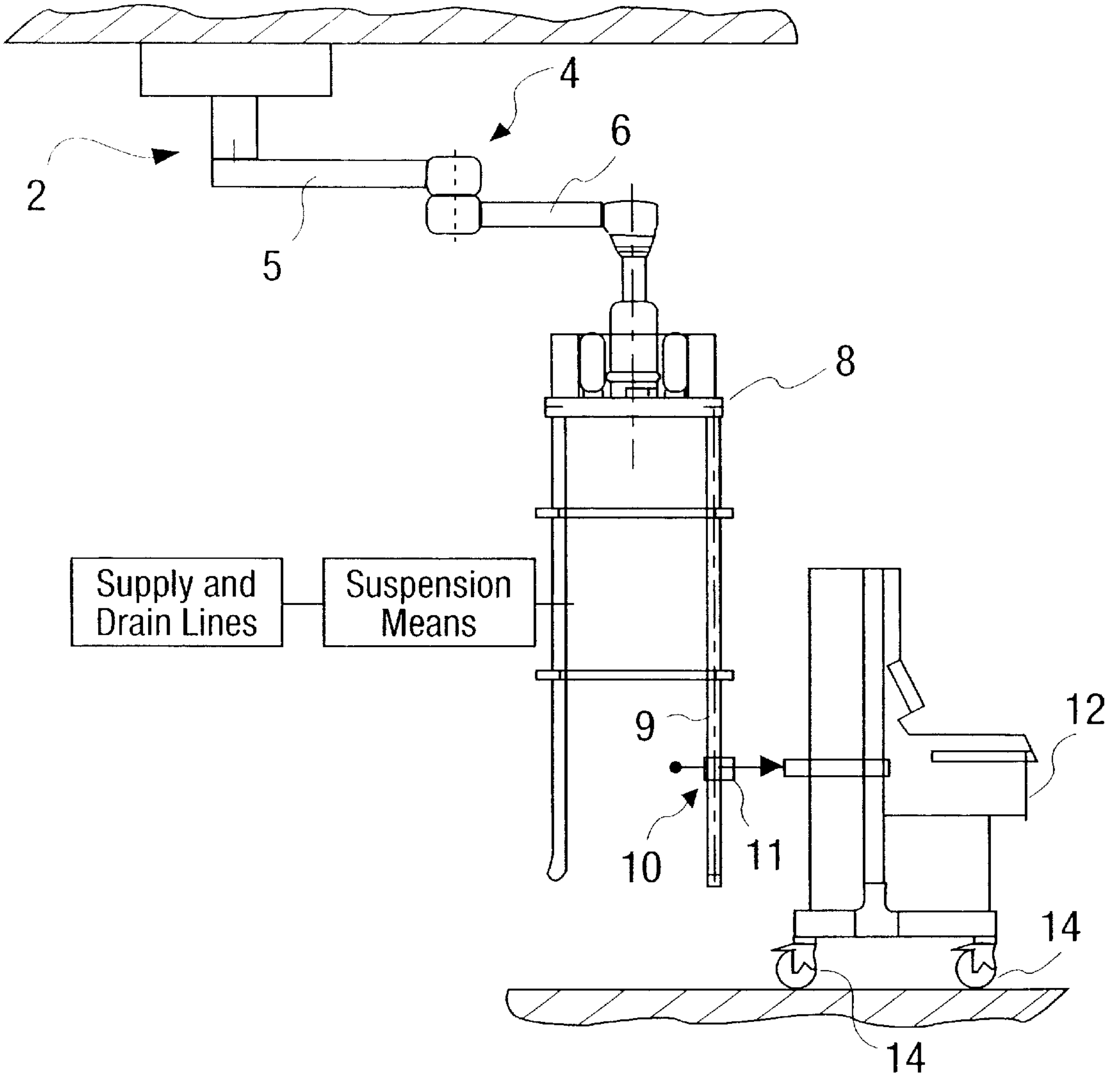
4
6
2
5
8
Supply and Drain Lines
Suspension Means
12
9
10
11
14
14

MOBILE MEDICAL SUPPLY DEVICE

FIELD OF THE INVENTION

The present invention pertains to a mobile medical supply device with a supply apparatus, especially an anesthesia apparatus, to which a plurality of supply lines and drain lines for supplying the patient are to be connected in operation. The lines may be a plurality of electrical, liquid-carrying and gas-carrying lines.

BACKGROUND OF THE INVENTION

Since the supply apparatus often must be moved during use, e.g., in an operating room or in an intensive care unit, the handling of the supply apparatus is complicated, because the supply and drain lines must be moved along in a coordinated manner during its movement.

In a prior-art supply device, the supply apparatus is provided with rollers, so that it can be moved on the floor. However, it is difficult in this case to ensure a coordinated joint movement of the supply and drain lines, which extend, on the one hand, from, e.g., stationary outlets in the operating room to the supply apparatus and, on the other hand, beginning from these to the patient. When the supply apparatus is moved, the personnel must ensure at the same time that the lines are moved along and do not hang in the room in a manner hindering or jeopardizing the work. To achieve this, the lines must be pulled along and laid over stationary suspensions. This makes the movement of such a movable supply apparatus very cumbersome for the personnel.

As an alternative design for a mobile supply device, it has been known that a ceiling fixture suspended from the ceiling of the medical work room may be provided, which lamp has a double arm rotatably suspended on the ceiling, at one end of which, which end faces away from the axis of rotation, a frame hanging above the floor of the room is suspended. The medical supply apparatus is hung into this frame, so that it is held freely floating in the room. The ceiling fixture with its double arm is provided with suspensions and guides, into which the supply and drain lines to the supply apparatus can be hung. To move the supply apparatus, the latter is displaced by the personnel, while the double arm rotates and/or a pivoting of the arms of the double arm takes place relative to one another. A simple movement of the supply apparatus is thus made possible in a simple manner, and the supply and drain lines suspended on the ceiling fixture are carried along automatically during movements of the supply apparatus. One drawback of this device is that both the suspension of the ceiling fixture and the double arm must be designed as a very stable unit and for a high load-bearing capacity in order for them to be able to carry the supply apparatus, which may have a considerable weight, freely floating in the room. The consequence of this is a high initial cost, on the one hand, and, on the other hand, high costs for the installation of the suspension of the ceiling fixture with the necessary load-bearing capacity. Another drawback is that the supply apparatus cannot be expanded with auxiliary apparatuses, because the frame provided for the supply apparatus has no place for this.

SUMMARY AND OBJECTS OF THE INVENTION

The primary object of the present invention is to provide a mobile medical supply device that is simpler in terms of its design and its installation than the above-mentioned one and also makes possible a simple operation during use and a simple following movement of the supply and drain lines to the medical supply apparatus during use.

According to the present invention, the medical supply device is provided with a medical supply apparatus movable on rollers on the floor as well as with a ceiling fixture, which has a multilink arm, which is to be rotatably suspended on a room ceiling and is directed essentially horizontally in the suspended state, wherein the links of the multilink arm are pivotably connected to one another. A frame, which is movable in a horizontal plane in the room due to rotation and movement of the multilink arm and which is provided with means for suspending the supply and drain lines, is suspended at one end of the multilink arm facing away from the axis of rotation. The supply apparatus is coupled with the frame by means of a mechanical connection means, and the mechanical connection means has clearance for vertical movements between the frame and the movable supply apparatus, so that unevennesses of the floor are compensated during the movement of the supply apparatus without load on the ceiling fixture.

Since the ceiling fixture in the device according to the present invention has to carry only the frame, whereas the supply apparatus rests on rollers on the floor, the ceiling fixture may be designed as a mechanically much simpler and lighter-weight ceiling fixture, because it can be designed for a substantially lower load-bearing capacity. This leads to considerably reduced manufacturing costs and installation costs for the ceiling fixture. At the same time, simple following movement of the supply and drain line s to the supply apparatus is guaranteed during its movement, because these lines may be suspended on the ceiling fixture.

Another advantage of the device according to the present invention is that the movable supply apparatus may be connected to expansion apparatuses, which may be fastened on or at the supply apparatus or may also be designed as movable apparatuses and may be coupled with the supply apparatus. The coupling of expansion apparatuses is not possible in the case of prior-art devices with a floatingly suspended supply apparatus.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawings:

The only FIGURE is a schematic side view of the mobile supply device.

DESCRIPTION OF THE PREFERRED EMBODIMENT

Referring to the drawings in particular, the invention comprises a supply device that has a ceiling fixture 2, which is firmly anchored in the ceiling of the medical work room and has a multilink arm. The multilink arm of the preferred embodiment has a double arm 4, which is rotatable on an anchoring around a vertical axis. The double arm 4 has two, essentially horizontally extending arms 5 and 6, which are pivotably connected to one another at their connection point. A frame 8 is suspended at the end of the arm 6 facing away from the axis of rotation of the ceiling fixture. The suspension of the frame 8 on the arm 6 is preferably designed such that it permits rotation of the frame around a vertical axis.

The frame 8 can be moved in a horizontal plane through the medical work room due to the rotation of the ceiling fixture 2 and the pivoting of the arms 5 and 6 of the double arm 4 in relation to one another and it can thus be brought, e.g., into a desired position at an operating table.

Furthermore, a medical supply apparatus 12 is provided, which can be moved on rollers 14 on the floor of the medical work room. The supply apparatus 12, e.g., an anesthesia apparatus, may be coupled with the frame 8 by means of a mechanical connection means 10. This mechanical connection means 10 is designed such that it permits vertical movements between the frame 8 and the supply apparatus 12, i.e., the connection means 10 can compensate relative movements between the supply apparatus 12 and the frame 8 due to its vertical clearance when the supply apparatus 12 is moving during the movement relative to the frame 8 because of unevennesses of the floor. As a result, any load on the ceiling fixture 2 and the frame 8 due to the weight of the supply apparatus 12 is avoided.

Futhermore, suspension means 16 for suspending the supply and drain lines 18 to the supply apparatus 12 provided on the frame 8.

The medical supply device can thus be moved in the medical work room by the personnel displacing the movable supply apparatus 12, while the coupled frame 8 moves along while the arms 5, 6 are rotated and/or pivoted in relation to one another. At the same time, the supply and drain lines to the supply apparatus 12, which are suspended on the frame 8, are moved along, so that the supply device can be moved by a single operator without any special precautionary measures for moving along the supply and drain lines.

To improve the mobility of the devices, the mechanical connection means between the frame 8 and the supply apparatus 12 preferably permits not only vertical relative movements, but also a pivoting movement of the supply apparatus 12 in relation to the frame 8 in a horizontal plane, i.e., the supply apparatus 12 can rotate around a vertical axis of rotation on the frame 8.

Such a mechanical connection means 10 may be formed, e.g., by a vertical bar 9, which is fastened to the frame and is completely or partially surrounded by a sleeve 11 connected to the supply apparatus 12, wherein the sleeve 11 is displaceable in the vertical longitudinal direction of the bar 9. Both a vertical mobility of the supply apparatus 12 in relation to the bar 9 on the frame 8 and rotation of the supply apparatus 12 around the bar 9 are thus possible.

While a specific embodiment of the invention has been shown and described in detail to illustrate the application of the principles of the invention, it will be understood that the invention may be embodied otherwise without departing from such principles.

What is claimed is:

1. A device, comprising:

a supply apparatus movable on rollers on a floor;

a plurality of supply and drain lines extending to and/or from the supply apparatus for connection with a patient;

a ceiling fixture with a multilink arm, said ceiling fixture being rotatably suspendable around a vertical axis on a room ceiling and being directed essentially horizontally in a suspended state;

a frame suspended at or adjacent an end of said multilink arm, said frame being movable in a horizontal plane due to rotation and movement of said multilink arm;

a supply line suspension means for suspending the supply and drain lines, said supply line suspension means being connected to said frame;

a mechanical connection means provided between said movable supply apparatus and said frame, said mechanical connection means providing clearance for vertical movements between said frame and said movable supply apparatus, whereby an unevenness of the floor is compensated during the movement of said supply apparatus without load on said ceiling fixture.

2. The supply device in accordance with claim 1, wherein said mechanical connection means allows rotation of said supply apparatus around a vertical axis.

3. The supply device in accordance with claim 2, wherein said mechanical connection means includes a bar portion of said frame having a longitudinal axis directed vertically and a sleeve connected to said supply apparatus, said sleeve being movable in a longitudinal direction of said bar.

4. The supply device in accordance with claim 1, wherein said mechanical connection means includes a bar portion of said frame having a longitudinal axis directed vertically and a sleeve connected to said supply apparatus, said sleeve being movable in a longitudinal direction of said bar.

5. A medical supply device for use in a space having a floor and a ceiling, the device comprising:

a supply apparatus movable on rollers on the floor;

a plurality of supply and drain lines extending from and connected to said supply apparatus;

a ceiling fixture with a multilink arm, said ceiling fixture being rotatably suspendable on the ceiling, said multilink arm moving essentially horizontally in a suspended state;

a frame suspended at or adjacent an end of said multilink arm, said frame being movable in a horizontal plane due to rotation and movement of said multilink arm;

a supply line suspension mechanism connected to said supply and drain lines and connected to said frame;

a mechanical connection provided between said movable supply apparatus and said frame, said mechanical connection allowing vertical movement between said frame and said movable supply apparatus, whereby an unevenness of the floor is compensated during the movement of said supply apparatus without load on said ceiling fixture.

6. The supply device in accordance with claim 5, wherein said mechanical connection allows rotation of said supply apparatus around a vertical axis.

7. The supply device in accordance with claim 5, wherein said mechanical connection includes a bar portion of said frame having a longitudinal axis directed vertically and a sleeve connected to said supply apparatus, said sleeve being movable in a longitudinal direction of said bar.

8. The supply device in accordance with claim 6, wherein said mechanical connection includes a bar portion of said frame having a longitudinal axis directed vertically and a sleeve connected to said supply apparatus, said sleeve being movable in a longitudinal direction of said bar.

9. The supply device in accordance with claim 1, wherein said supply apparatus is an anesthesia apparatus.

10. The supply device in accordance with claim 5, wherein said supply apparatus is an anesthesia apparatus.

* * * * *